(12) United States Patent
Barbieri et al.

(10) Patent No.: US 8,834,636 B2
(45) Date of Patent: Sep. 16, 2014

(54) APPARATUS AND METHOD FOR THE CONTINUOUS PICKLING OF STEEL STRIP

(75) Inventors: Philippe Barbieri, Lyons (FR); Sandra Crowther, Lyons (FR); Jean-François Clavel, Genilac (FR); Jacques Leroyer, Vienne (FR)

(73) Assignee: Siemens VAI Metals Technologies SAS, Saint-Chamond (FR)

( * ) Notice: Subject to any disclaimer, the term of this patent is extended or adjusted under 35 U.S.C. 154(b) by 780 days.

(21) Appl. No.: 12/809,719

(22) PCT Filed: Nov. 28, 2008

(86) PCT No.: PCT/FR2008/001655
§ 371 (c)(1),
(2), (4) Date: Jun. 21, 2010

(87) PCT Pub. No.: WO2009/098401
PCT Pub. Date: Aug. 13, 2009

(65) Prior Publication Data
US 2010/0269854 A1 Oct. 28, 2010

(30) Foreign Application Priority Data
Dec. 21, 2007 (FR) ...................................... 07 60222

(51) Int. Cl.
*C23G 1/02* (2006.01)
*C23G 3/02* (2006.01)
*B08B 7/04* (2006.01)

(52) U.S. Cl.
CPC ... *C23G 1/02* (2013.01); *C23G 3/02* (2013.01)
USPC .............................. 134/3; 134/18; 134/122 R (58) Field of Classification Search
USPC ................ 134/3, 15, 18, 28, 32, 41, 9, 122 R
See application file for complete search history.

(56) References Cited

U.S. PATENT DOCUMENTS

| | | | | |
|---|---|---|---|---|
| 4,144,149 A * | 3/1979 | Bollhalder et al. | ........... | 588/303 |
| 4,886,590 A * | 12/1989 | Tittle | ............................. | 204/232 |
| 5,175,502 A | 12/1992 | Rodabaugh et al. | | |
| 5,875,831 A | 3/1999 | Nohara et al. | | |
| 6,096,137 A * | 8/2000 | Mabuchi et al. | ................... | 134/3 |
| 6,396,280 B1 | 5/2002 | Nonaka et al. | | |
| 6,419,756 B1 | 7/2002 | Schlechter | | |

(Continued)

FOREIGN PATENT DOCUMENTS

| | | | |
|---|---|---|---|
| EP | 1106713 A2 * | 6/2001 | |
| FR | 2892191 A1 * | 4/2007 | |

(Continued)

OTHER PUBLICATIONS

Machine translation of EP1106713.*

(Continued)

*Primary Examiner* — Michael Kornakov
*Assistant Examiner* — Douglas Lee
(74) *Attorney, Agent, or Firm* — Laurence A. Greenberg; Werner H. Stemer; Ralph E. Locher (57) ABSTRACT

The pickling of a continuously running steel strip and, more particularly, a pickling method, includes centralized control of all of the pickling operations. The invention further includes an apparatus for implementing the pickling process.

24 Claims, 4 Drawing Sheets

(56) References Cited

U.S. PATENT DOCUMENTS

| | | | |
|---|---|---|---|
| 7,623,226 B2 | 11/2009 | Legoupil | |
| 2002/0130666 A1 | 9/2002 | Nonaka et al. | |
| 2002/0139391 A1* | 10/2002 | Simpson | 134/3 |
| 2004/0149323 A1 | 8/2004 | Takeuchi et al. | |
| 2009/0245622 A1 | 10/2009 | Janin et al. | |

FOREIGN PATENT DOCUMENTS

| | | |
|---|---|---|
| FR | 2893519 A1 | 5/2007 |
| JP | 56136982 A | 10/1981 |
| JP | 2000297390 A | 10/2000 |
| RU | 2125616 C1 | 1/1999 |
| WO | 2006134259 A1 | 12/2006 |

OTHER PUBLICATIONS

Abstract of FR2892191.*

Excerpt of J. Gavina et al. article (J. Gavina, G. Guzman, P. Barbieri and J. Leroyer (2006). VAI pickling for ultra thin hot strip in ACB. Revue de Métallurgie, 103, pp. 352-356. doi:10.1051/metal:2006136).*

Abstract of J. Gavina et al. article (J. Gavina, G. Guzman, P. Barbieri and J. Leroyer (2006). VAI pickling for ultra thin hot strip in ACB. Revue de Métallurgie, 103, pp. 352-356. doi:10.1051/metal:2006136).*

* cited by examiner

APPARATUS AND METHOD FOR THE CONTINUOUS PICKLING OF STEEL STRIP

BACKGROUND OF THE INVENTION

Field of the Invention

The invention relates in general to the pickling of steel strip running continuously through a pickling apparatus, and more specifically a pickling method which includes centralized control of all of the pickling operations and the apparatus for implementing said pickling.

In their production processes, the steel strips are hot rolled at temperatures that can reach nearly 1200° C. at the end of rolling, and then cold rolled. After hot rolling, the steel strips are cooled by spraying water onto the faces of the rolled strips, and they are wound at temperatures of up to 800° C. onto coils.

During hot rolling, an oxidizing reaction with the water spray forms an iron-oxide layer known as "scale", such that following hot rolling, the steel strips are covered by a relatively thick and hard layer of scale. Oxidation continues as the coils are air cooled. The different temperatures and sources of oxidation result in the presence of three iron oxides in the scale. This scale must be removed before final cold rolling, as otherwise it would encrust onto the metal and significantly alter its surface condition and its suitability for deep drawing. Furthermore, as the scale layer is extremely hard, its presence on the steel strips could cause very rapid wear of the cold-rolling rollers.

Systems comprising specialized lines that subject strips running continuously through tanks containing acid pickling solutions to chemical pickling are classically used for pickling hot-rolled strips.

In the oldest systems, the pickling solutions are solutions of sulfuric acid. However, hydrochloric acid-based pickling solutions are used nowadays for environmental and productivity reasons.

Figure 1:
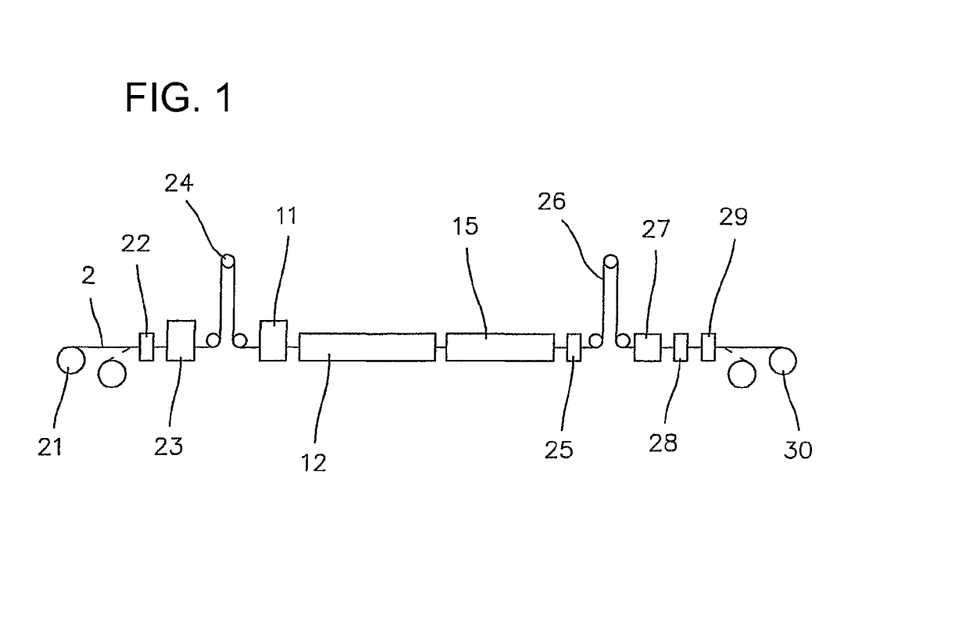
FIG. 1 is a schematic drawing of a first example of the continuous pickling line apparatus known in the prior art.

An example of a classical continuous pickling line apparatus 1 is shown in FIG. 1. It is a pickling apparatus 1, comprising:
- a fragmentation system 11 for the oxides that have formed on the surface of the steel strip 2 during hot rolling of that strip 2, to accelerate the subsequent pickling process,
- an actual pickling system 12 comprising a plurality of pickling tanks (not shown in FIG. 1) for the acid to corrode these oxides, and
- a rinsing unit 15 to remove the acid (in particular hydrochloric acid) and iron chlorides present on the surface of the strip 2, the fragmentation system 11, the pickling system 12 and the rinsing unit being arranged in series such that the strip 2 being pickled passes them successively as it runs continuously through the pickling apparatus 1.

The apparatus 1 shown in FIG. 1 also includes:
- a set of strip uncoilers 21 operating alternately, a welder 23 and a first accumulation system 4, which are arranged in series upstream of the fragmentation system 11, and
- a drier 25, a second accumulation system 26, an edge shear 27, an oiler 28, a shear 29 and a set of coilers 30, which are also arranged in series but downstream of the pickling system 12.

In operation, the strip 2 being pickled is uncoiled by the strip uncoilers 21 and passes the shear 22 which crops the head of the strip 2. The strip 2, passing the welder 23, is then welded to the tail of the strip previously cropped by the shear 22. The accumulation system 24 then enables the strip 2 to be accumulated, and then returned downstream, i.e. immediately upstream of the fragmentation system 11, when the tail of the previous strip and the strip 2 being pickled are welded. The strip 2 then passes the oxide fragmentation system 11, commonly known as an oxide breaker. This fragmentation system 11 in particular enables the mechanical fragmentation of the scale formed on the strip 2 during the hot-rolling phase, which facilitates and speeds up the acid pickling of the strip 2 which immediately follows this mechanical fragmentation. Then, having passed the fragmentation system 11, the strip 2 being pickled runs continuously through the pickling tanks of the pickling system 12, which are each filled with a churning pickling solution. The acid pickling of the strip 2 is then realized by dipping, and a pickled strip 2 is obtained.

Then, having run through the tanks of the pickling system 12, the strip 2 is then rinsed in the rinsing unit 15, then dried in the drier 25. The second accumulation device 26 enables the strip 2 to run continuously through the pickling apparatus 1 during the cropping and coiler 30 loading operations.

The edge shear 27 is used to remove the edges of the strip to ensure there are no "edge" defects, such as cracks, and to guarantee a continuous strip width. The oiler 28 is used to protect the pickled sheet against oxidation. The shear 29 crops the strip 2 at the end of the coil, and the coilers 30, which operate alternately, coil the pickled strip 2.

Figure 2:
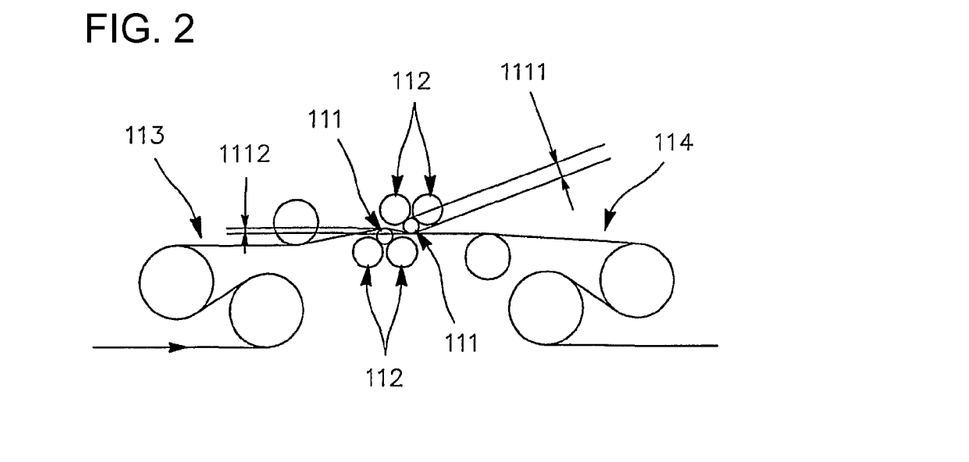
FIG. 2 is a schematic drawing of an example of an oxide fragmentation system known in the prior art and intended for use in a continuous pickling line apparatus.
Figure 3:
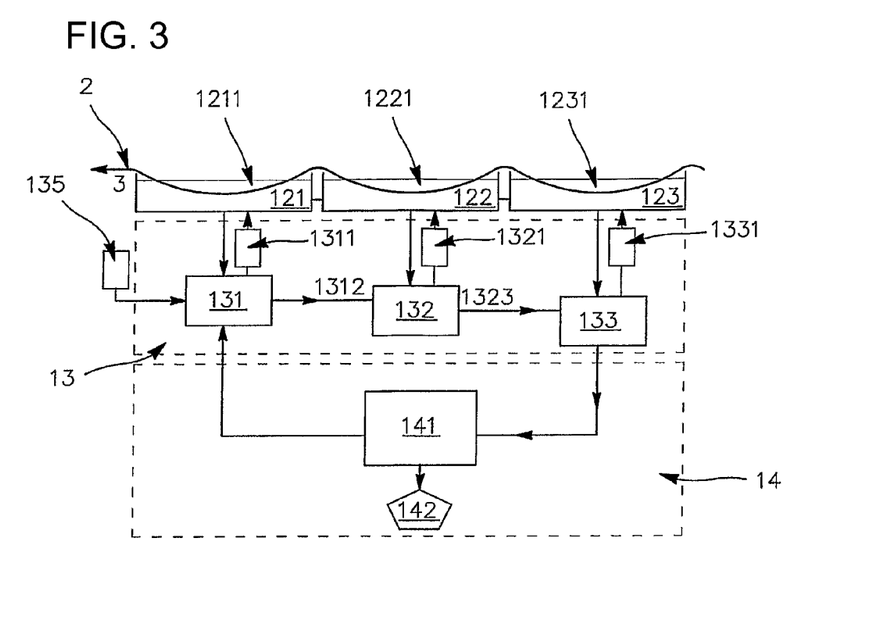
FIG. 3 is a schematic drawing of an example of a pickling system known in the prior art and intended for use in a continuous pickling line apparatus.

The oxide fragmentation operation, which is intended to speed up the overall strip pickling operation, is typically realized in an oxide fragmentation system 11, such as the one shown schematically in FIG. 1 and in greater detail in FIG. 2. This system 11 enables the fragmentation of the scale layer using a technique known as "tension leveling", which involves alternately bending the strip 2 on work rolls 111, which are held by supporting rollers 112, the strip 2 being subjected to elongation by the input 113 and output 114 tensioners. Elongation may reach 2%. The example fragmentation system 12 shown FIG. 3 is one of the most commonly used systems on continuous pickling lines. Such a system 11 also helps to improve the flatness of the strip 2 being pickled.

The actual pickling operation involves causing the iron oxides ("scale") to react with the acid pickling solution. Different chemical reactions occur in this pickling solution depending on the chemical characteristics of the scale layer.

In fact, when the strip is hot, between the output of the final finishing stand of the hot mill and the coiler, the scale has a structure made up of layers of protoxide FeO, magnetite $Fe_3O_4$ and a little hematite $Fe_2O_3$. When the coils are cooling in ambient air, the strip heads and tails and the edges cool rapidly, and the scale develops into an $Fe_3O_4$ and $Fe_2O_3$ structure. As the rest of the strip cools more slowly, the scale forming on it is essentially an $Fe_3O_4$—Fe eutectic composition potentially with a little residual FeO.

Thus, during pickling in a pickling solution based on hydrochloric acid, the following chemical reactions occur:

$$FeO + 2HCl \rightarrow FeCl_2 + H_2O \tag{1}$$

$$Fe_2O_3 + 6HCl \rightarrow 2FeCl_3 + 3H_2O \tag{2}$$

$$Fe_3O_4 + 8HCl \rightarrow FeCl_2 + 2FeCl_3 + 4H_2O \tag{3}$$

$$Fe + 2HCl \rightarrow FeCl_2 + H_2 gas \tag{4}$$

$$2FeCl_3 + Fe \rightarrow 3FeCl_2 \tag{5}$$

These reactions demonstrate that during pickling the pickling solution has an overall tendency to become less acidic and to become charged correspondingly with iron chlorides. As a continuous pickling process requires the characteristics of the pickling solution to be kept as constant as possible, it must necessarily be regenerated in "regeneration" tanks, which are arranged in line with the pickling installation and which work by injection into a furnace or reactor. Moreover, inhibitors are used to limit the acid corrosion on the bare steel, in particular if the strip stops in the bath.

The loss of acidity in the pickling solution, the flow of pickling solution drawn by the strip down through the pickling apparatus, the need to renew and to ensure the best possible concentration balance between successive tanks in the pickling system have led to the adoption of a pickling system such as the one shown in FIG. 3. This comprises a plurality of pickling tanks 121, 122, 123 (usually at least 3), which are each filled with pickling solution 1211, 1221, 1231 made up notably of sulfuric acid or hydrochloric acid.

These tanks 121, 122, 123 are arranged in series one behind the other following the longitudinal running direction of the strip 2, such that the strip runs successively from one to the other (in this case from tank 123 to tank 121 via tank 122).

The control means for movement of the strip 2 (not shown in FIG. 3), for example a coiler, are classically arranged at the output of the pickling apparatus 1. These control means enable the strip 2 to be driven in the running direction so that it passes successively through the different pickling tanks 121, 122, 123 forming inside each of them a concave curve oriented upwards (known as a "catenary" curve) which is immersed in the pickling solution 1211, 1221, 1231 contained in each of the tanks 121, 122, 123.

In addition to the pickling tanks 121, 122, 123, the pickling apparatus shown in FIG. 1 includes a recirculation circuit 13 and a regeneration circuit 14 for the pickling solution 1211, 1221, 1231.

The recirculation circuit 13 includes a plurality of storage tanks 131, 132, 133 that are each linked to a pickling tank 121, 122, 123 by means of units for pumping and heating using exchangers 1311, 1321, 1331.

The storage tanks 131, 132, 133 are also connected by ducts 1312, 1323, such as to arrange them in the pickling apparatus in the direction opposite the running direction 3 of the strip 2 in the pickling apparatus 1.

The regeneration circuit 14 includes a pyrohydrolysis unit 141 to transform the iron chlorides formed during acid corrosion into iron oxides, and a recovery tank 142 to collect oxides in tanks.

The pyrohydrolysis unit 141 is connected to the first storage tank 133 and to the last storage tank 131 encountered in the running direction 3 of the strip 2 in the apparatus 1.

Moreover, the recovery tank of the tanks 142 is only connected to the pyrohydrolysis unit 141, such that the iron chloride-rich pickling solution is captured in the first circulation tank 133, then regenerated in the pyrohydrolysis unit 141 by means of reactions 6, 7, where the iron chlorides are transformed into oxides:

(6)

$$2FeCl_2 + 2H_2O + \tfrac{1}{2}O_2 \rightarrow Fe_2O_3 + 4HCl \qquad (6)$$

(7)

$$2FeCl_3 + 3H_2O = Fe_2O_3 \rightarrow 6HCl \qquad (7)$$

The pickling solution thus regenerated is then returned to the last circulation tank 131.

The acid concentration balances between the different tanks 121, 122, 123 are defined in a known manner by the flow of pickling solution 1211, 1221, 1231 moved by the strip 2 running from tank to tank (i.e. from tank 123 to tank 121 via tank 122), and by the rate of reverse cascade between the storage tanks 131, 132, 133 (i.e. from tank 131 to tank 133 via tank 132).

Extra regenerated acid and, if necessary, new acid 135 is added to the circulation tank 131.

The free-acid concentration is therefore highest in the last pickling tank 121 where it can reach 200 g/l and drops in the upstream tanks 122, 123, where it only reaches a few tens of g/l in the first tank 123. Correspondingly, the pumping and reheating unit 1331 makes it possible to maintain a heating power that is greater in the first tank 123 in order to reheat the strip 2 and to ensure it is pickled despite the low acid concentration.

Once the scale has been eliminated by fragmentation of the scale by acid corrosion, the acid solution may start to corrode the bare strip 2, in particular if the strip 2 stops running and remains for an extended period in the pickling tanks 121, 122, 123. This unwanted corrosion, commonly known as "over pickling" has the following effects:

Loss of weight,
Variation in surface roughness,
Change of coloration,
Creation of surface marks,
Excessive generation of hydrogen, which may accumulate locally and create an explosion risk.

To avoid this, an inhibitor is usually added to the pickling solution 1211, 1221, 1231. Although a correct initial titration of this inhibitor does prevent all risk of over-pickling during normal operation of the apparatus 1, it may be inadequate if the strip stops running and remains for an extended period in the pickling tanks.

Following acid pickling, the strip 2 must be rinsed to remove the acid and the iron chlorides present on the surfaces of the strip 2. Rinsing is generally performed in a rinsing unit 15, such as the one shown in FIG. 4. This is a rinsing unit classically used in continuous pickling lines.

Figure 4:
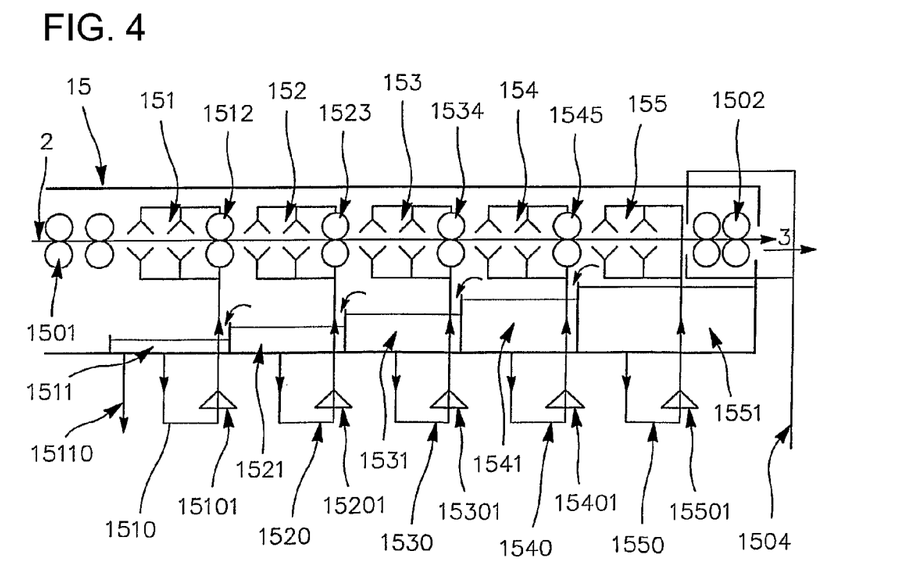
FIG. 4 is a schematic drawing of an example of a rinsing unit 15 known in the prior art and intended for use in a continuous pickling line apparatus.

This rinsing unit 15 includes:
batteries of spray bars 151, 152, 153, 154, 155, that are arranged such that they can spray both faces of the strip 2 being pickled as it is running through the rinsing unit 15,
a plurality of flow tanks 1511, 1521, 1531, 1541, 1551, each of which is arranged beneath a spray bar 151, 152, 153, 154, 155 respectively to recover the water sprayed by the bars 151, 152, 153, 154, 155, each of the flow tanks 1521, 1531, 1541, 1551 overflowing into its neighboring tank forming a cascade flowing in the direction opposite to the running direction 3 of the strip 2, and
Roller drier devices 1501, 1502 placed at the entrance and exit of the rinsing unit 15, as well as roller drier devices 1512, 1523, 1534, 1545 placed between each battery of bars 151, 152, 153, 154, 155.

Rinsing is usually performed by a counter-current cascade operating as follows: the strip 2 passes through the rinsing unit 15, where it is sprayed, on both faces, with water, preferably demineralized, by batteries of spray bars 151, 152, 153, 154, 155. The roller drier devices prevent the strip 2 from drawing acid diluted in the water.

The water flowing beneath each battery 151, 152, 153, 154, 155 is recovered in its corresponding flow tank 1511, 1521, 1531, 1541, 1551, the overflow of each tank 1511, 1521, 1531, 1541, 1551 flowing into its neighboring tank in the direction opposite to the running direction 3 of the strip 2.

Each flow tank 1511, 1521, 1531, 1541, 1551 is also fitted with a recirculation circuit 1510, 1520, 1530, 1540, 1501, 1502 each of which includes a pump 15101, 15201, 15301, 15401, 15501. The now acid-rich rinsing water 15510 is recovered in the first flow tank 1511 encountered in the running direction 3 of the strip 2, then discharged. Extra demineralized water 15510 is situated in line with the final flow tank 1551 encountered.

Generally, following the acid pickling and rinsing stages, the surface characteristics of a pickled and rinsed strip are analyzed. This makes it possible to make an initial assessment of the quality of the operations performed and, depending on these results, to correct or optimize certain parameters such as the strip running speed V and parameters related to the oxide fragmentation, acid pickling and rinsing processes.

In general, these surface characteristics are defined in accordance with the following characteristics:

- a well pickled strip has a visibly uniform appearance with minor variations in roughness over the width and length of the strip,
- an "under pickled" strip has brown or grey marks that are quite easy to detect and located across the width of the strip, there being major variations in surface condition between the correctly and inadequately pickled zones,
- an "over pickled" strip has a grey appearance, for example following a prolonged stoppage in the pickling tanks. This grey appearance is easy to detect on visual inspection.

However, more subtle visual defects due to inadequate settings for running speed, inhibitor concentration, temperature or acid concentration may not be visible to the naked eye and require high-performance image capture and analysis means.

Roughness variation analyses may also be used in addition to appearance analysis.

Consequently, a continuous pickling operation for steel strip in an acid medium on a continuous pickling line, such as the one shown in FIG. 1, requires the management of a significant number of adjustable parameters relating to the running speed of the strip in the apparatus 1, the performance of oxide fragmentation in the fragmentation system 11, the performance of actual pickling in the pickling system 12, and the performance of rinsing in the rinsing unit 15.

Japanese patent application JP 56-136982 proposes a control system limited to measuring only the density of the pickling solution which controls the opening and closing of a valve for adding new acid. The acid concentration is calculated solely using this measurement of the density of the pickling solution, applying empirical formulas. Other acid bath control parameters, such as temperature, are not taken into account. The control system described in JP 56-136982 is however inadequate: firstly, the reduction in acid concentration due to the chemical reactions 1 to 4 mentioned above is a slow process, and, secondly, the addition of fresh acid involves a significant time constant, resulting in very significant fluctuations in the controlled variable.

In this field, U.S. Pat. No. 6,396,280 is also known, which describes a control system for acid concentration, with which it is possible to continuously measure acid concentration in two consecutive tanks, which makes it possible to measure extra acid doses. Although similar in principle to patent JP 56-136982, the American U.S. Pat. No. 6,396,280 claims to limit the fluctuations in acid concentration. However, only one parameter is monitored, and the result of the pickling operation is not taken into account as a control parameter.

Patent application US 2002/0130666 describes a complete measurement system outside the pickling tank. This system, which is fitted with a temperature sensor and a conductivity meter, makes it possible to measure the density of the pickling solution by means of variations in the level of liquid in a column. This system effectively makes it possible to change the performance of continuous pickling, but it does not identify the relative impact of concentrations of acid and iron chlorides in the measurements.

On the other hand, American U.S. Pat. No. 5,175,502 describes a more precise system intended to identify the effects of the acid concentration and iron chloride concentrations by measuring, at a controlled temperature, the density of the undiluted pickling solution coming from a pickling tank, and the conductivity of the same pickling solution, but diluted in a controlled manner with water. Conductivity varies little with the iron chloride concentration for low acid concentrations (for example around 25 g/l). Conductivity measured in this way is then considered to be independent of the iron chloride content, and therefore representative only of HCl content. Knowing the dilution rate used for the measurement, it is then easy to extrapolate the acid concentration in the pickling tank and to calculate the iron-chloride concentration. However, the techniques implemented to measure this acid concentration do not allow this concentration to be controlled.

There is nothing in the systems of the prior art described above that make it possible to optimize the pickling operation as a whole.

To overcome this, the person skilled in the art knows a pickling method controlled by a global process that manages the pickling operation as a whole. Thus, U.S. Pat. No. 6,419,756 describes a method for pickling a rolled metal strip running through a pickling apparatus, which includes:

- Adjustment of the pickling parameters by an operator, for example the temperature of the pickling solution
- Using an optical measuring instrument to measure defects in the metal strip, which are sorted into different categories of defects and counted by a classifier to determine the frequency of occurrence of these types of faults;
- Sending these defect category occurrence frequencies to an evaluator, which may be a fuzzy evaluator, a neural network or a neural fuzzy evaluator; and finally
- Evaluation by the evaluator of the result of pickling, which is a function of the pickling adjustment parameters, on the basis of which the evaluator determines instructions for at least one of the pickling adjustment parameters.

Such a system has the drawback of acting on any one of the adjustment parameters. In the embodiment described in U.S. Pat. No. 6,419,756, this is preferably the temperature of the pickling solution. Such a modification has the major drawback of not having an immediate effect on account of the inertia inherent in a pickling apparatus.

BRIEF SUMMARY OF THE INVENTION

This invention therefore relates to a pickling method that overcomes the drawbacks of the prior art by implementing a global control process that acts directly on the strip running speed by reducing it in steps, and that does not change the adjustment parameters of the pickling. This invention also relates to an apparatus for implementing the method according to the invention.

More specifically, this invention relates to a pickling method for a metal strip running continuously through a continuous pickling line apparatus, which includes successively a fragmentation stage for oxides formed on the surface of said strip during hot rolling, an acid pickling stage, a strip rinsing stage, and a drying stage, the strip being driven at a running speed V in said apparatus in a longitudinal running direction perpendicular to the width of the strip, the strip running speed V being controlled by an uncoiling and coiling unit, and each of the stages of pickling being controlled by actuators that can act on the adjustment parameters of the pickling line, the action or absence of action of an actuator on a given adjustment parameter being identified by a status datum.

The pickling method according to the invention also includes a global process for controlling pickling, which implements:
- the continuous measurement of at least some of the pickling adjustment parameters, said measurement being implemented during pickling;
- a command phase which is implemented during pickling, during which the global control process defines and sends optimized command instructions to all of the actuators using a predictive control system; and
- continuous inspection of the surface of the strip.

According to the invention, the global process for controlling the pickling method includes:
- a prior preparation phase, which is implemented upstream or at the start of pickling, during which the global control process defines and sends pre-adjustment instructions to all of the actuators using an analytical model, which may be associated with a predictive control system;
- the continuous calculation of at least some of the pickling adjustment parameters, said calculation being implemented during pickling; and
- the continuous inspection of the surface of the strip defines and sends, in the event of under-pickling, an alarm instruction to the command phase, which reduces stepwise the strip running speed V to a corrected running speed $V_{cor}$, the running speed V being reduced stepwise until this defect is no longer detected and no longer triggers an alarm instruction.

In this invention, actuator status datum means a datum that contains the operating or not-operating adjustment status of the actuator.

In this invention, analytical model means a model of the adjustment parameters, that is realized either using equations or predetermined pre-adjustment tables.

The use of an analytical model and a predictive control system has the advantage of making it possible to determine pickling speeds as a function of the adjustment parameters and the measurements of these parameters more precisely than with neural or fuzzy or neural fuzzy models, as in U.S. Pat. No. 6,419,756, and without the need for learning.

Advantageously, the predictive model of the global control process corrects the command instructions sent to all of the actuators apart from the strip running speed V, as a function of the correction made to the running speed $V_{cor}$, and such as to maintain the quality of the evaluation made during inspection of the surface of the strip.

Advantageously, the continuous inspection of the surface of the strip also results in the event of detection of defective rinsing, in a stepwise pH adjustment of the rinsing water, until the defect is no longer detected.

Advantageously, calculation makes it possible to determine the acid and iron concentrations in the pickling solution, that are used during acid pickling.

Advantageously, the preparation phase includes the following operations:
- receiving status data from the actuators, operating data, and target values for the adjustment parameters established by the analytical model to optimize strip pickling;
- establishing pre-adjustment instructions for each actuator;
- sending each actuator these pre-adjustment instructions;
- establishing the input data for the command phase;
- sending this input data to the command phase.

In this invention, operating data means the data on the strip to be pickled, the size of the strip, the steel grade of the strip, or even data on the scale formed during hot rolling (nature of oxides formed, quantity, for example).

According to one particularly advantageous embodiment of the preparation phase of the method according to the invention, the analytical model includes an analytical sub-model associated with each actuator to define said pre-adjustment instruction for the adjustment parameter on which the related actuator acts.

Advantageously, the command phase includes the following operations:
- receiving continuously and in real time status data from the actuators, information from the measurement and calculation means, and input data for the command phase established during the preparation phase;
- establishing command signals optimized for each actuator; and
- sending said command signals to the actuators.

According to one particularly advantageous embodiment of the command phase of the method according to the invention, the predictive control system includes a primary adjustment loop to check the optimum operation of each actuator on the command instruction sent to it.

Advantageously, the strip inspection phase includes optical inspection of the appearance of the surface of the strip and measurement of the variation of at least one characteristic of the surface condition of the strip.

Notable examples of characteristics of the surface condition of the strip include average roughness Ra, maximum roughness Rm (peak-to-peak value) and the number of peaks per cm.

Preferably, optical inspection (5001) of the appearance of the surface of the strip (2) and the variation measurement of the surface condition (5002) of the strip (2) include learning suspect zones with reference to a library of images and/or data enabling a distinction to be made between over-pickling defects, under-pickling defects, or the absence of defects.

This invention also relates to a continuous line apparatus for pickling a hot-rolled metal strip running continuously in said apparatus, said apparatus including:
- a fragmentation system for oxides formed on the surface of the strip, said oxide fragmentation system being adjustable by means of fragmentation adjustment parameters,
- a pickling system, which is adjustable using pickling adjustment parameters, and
- a rinsing system, which is adjustable using rinsing adjustment parameters,
- a drying system, and
- a set of means for measuring and calculating the adjustment parameters of said apparatus,
- a set of actuators, intended to act on the adjustment parameters of said apparatus.

According to the invention, the continuous pickling line apparatus also includes:
a centralized command system to optimize pickling of the metal strip, said command system including:
- a preparation module intended to receive information from all of the measurement and calculation means and the actuators, and to define and send pre-adjustment instructions to all of the actuators,
- a command module intended to receive information from all of the measurement and calculation means and the actuators, and to define and send optimized command instructions to all of the actuators, and
- a strip inspection system arranged at the output of the rinsing system, said inspection system being able to define and send an alarm instruction to the command module to act on the strip running speed V.

Advantageously, the inspection system is also able to define and send a command instruction to the command module to act on the rinsing adjustment parameters.

Advantageously, the set of measurement and calculation means includes:

a set of measurement means including means for measuring the strip running speed V, means for measuring the adjustment parameters for oxide fragmentation, means for measuring at least some of the adjustment parameters for pickling, and means for measuring the adjustment parameters for rinsing, and means for calculating at least some of the adjustment parameters for pickling.

Advantageously, the calculation means are able to determine the concentrations of acid and ferrous ions in the pickling solution used in the pickling system.

Advantageously, the set of actuators includes fragmentation actuators intended to act on the oxide fragmentation adjustment parameters, pickling actuators intended to act on the pickling adjustment parameters, and rinsing actuators intended to act on the rinsing adjustment parameters.

The pickling apparatus according to the invention enables the method according to the invention to be implemented.

Thus, if the method according to the invention is implemented in the apparatus according to the invention, the preparation phase of the method according to the invention is performed by the preparation module, which establishes, using the analytical model of the pre-adjustment instructions for the different actuators of the apparatus according to the invention, on the basis of the status data generated for the different actuators, operating data concerning the strip being pickled, and target values for the adjustment parameters.

In this invention, target values means the optimum values of the adjustment parameters that the global control process is intended to achieve.

Some of the pickling adjustment parameters are calculated using calculation means in the pickling apparatus according to the invention. These means may advantageously make it possible to determine, on the basis of density and conductivity measurements of the pickling solution in the storage tanks, the acid and iron concentrations of the pickling solution in these storage tanks.

Some of the pickling adjustment parameters are measured, during pickling, by the set of different measurement means placed on the pickling line.

The command phase is performed by the command module which, on the basis of status data from the actuators, information from the measurement and calculation means, and input data from the predictive control system established during the preparation phase, establishes command instructions that it sends to the different actuators on the pickling line, from which it receives status data in response, which are corrected on each iteration of the global control process.

The inspection phase of the surface of the strip is performed by the surface inspection system of the apparatus according to the invention, which is independent of the centralized command system.

This surface inspection system may advantageously include:

a system for inspecting the appearance of the surface of the strip, and which in particular makes it possible to determine the presence of marks on the surface of the strip, as well as their color, location and size, and a system for measuring surface condition, which makes it possible in particular to measure variation in at least one characteristic of the surface condition of the strip such as mean roughness Ra, maximum roughness Rm or number of peaks per cm.

According to one particularly advantageous embodiment of the present invention in the case of under-pickling, if only one of the surface appearance inspection system and the surface condition measurement system detects a defect and sends an alarm instruction to the command module which sends it to the operator, which only acts on the strip running speed V if the other of the surface condition measurement system and the surface appearance inspection system also detects said defect.

The strip surface appearance inspection system, useable in the apparatus according to the invention, may principally comprise:

a system for lighting the running strip such as the one described in French patent application FR 2892191, an image capture system, for example made up of a CCD camera such as the one described in French patent application FR 2893519, and an image processing function (FTI) to eliminate disturbances such as uneven lighting or light reflections, a grey-threshold or contour detection function (FD), a photometric and morphological characterization and extraction function for suspect zones (FE), a learning-based identification and classification function (FCI) for suspect zones with reference to an image library, capable of distinguishing "under pickling" defects, "over pickling" defects, previously described intrinsic defects in the steel strip, or the absence of any defects.

The surface appearance inspection system of the apparatus according to the invention makes it possible to detect pickling defects in the surface of the strip, such as over-pickling or under-pickling, or marks that remain after rinsing.

The lighting system of the surface appearance inspection system may advantageously include a strip light capable of lighting the entire width of the strip within at least one band of the visible spectrum and a color CCD camera capturing the light reflected by the strip.

The processing function (FTI) of this surface condition inspection system is used to eliminate disturbances such as uneven lighting or light reflections, from grey-threshold or contour detection functions and photometric and morphological characterization and extraction functions for suspect zones.

Finally the learning-based identification and classification function of suspect zones with reference to an image library of this system is used to identify "under pickling" defects, "over pickling" defects, intrinsic defects in the steel strip, or the absence of any defects.

The strip surface appearance inspection system according to the invention makes it possible to continuously examine the entire width of the running strip. The system described in international patent application WO2006/134259 can be used as the surface appearance inspection system.

Furthermore, the surface condition measurement system useable in the apparatus according to the invention may principally comprise an optical device, which is provided with the following functions:

a signal processing function (FTS) making it possible to detect variations in at least one profile characteristic (case 1), scatters characteristic (case 2) or reflected light spectrum characteristic (case 3) in suspect zones, a learning-based suspect-zone classification function (FC) with reference to a database, that is able to distinguish between defects and an absence of defects.

This surface condition measurement system makes it possible to continuously examine at least one line situated in the middle of the width of the running strip, and preferably three lines, one of which being situated in the middle of the strip width and the other two in a zone situated between one third and one quarter of the strip width from each edge of the pickled strip.

The optical system recommended for use in the strip surface condition measurement system according to the invention is a linear or spot laser triangulation scanner, using either profile measurement (case 1) or scatter (case 2), or, alternatively, an axial chromatic aberration optical device (case 3).

If a profile-measurement laser triangulation scanner device is used, it evaluates the surface condition of the pickled strip by measuring the profile of the illuminated surface by laser beam.

The beam of the laser scanner device may be a line (known as a linear laser scanner) or a spot (known as a spot laser scanner).

If a scatter-based laser triangulation scanner device is used, it evaluates the surface condition of the pickled strip by emitting at least two beams at different angles of incidence, the surface condition of the pickled strip is then evaluated by detecting the difference in the beam diffraction caused by the illuminated surface.

If an optical axial chromatic aberration system is used, it evaluates the surface condition of the pickled strip by spectral analysis of the light focused on the surface lit with white light by the optical device.

The optical device of the surface condition measurement system according to the invention is advantageously fixed above the center of the pickled strip.

According to a first particularly advantageous embodiment of the invention, two axial chromatic aberration optical, scatter laser or laser scanner systems are used, which are preferably located above the running strip, at a distance from its edges of between one third and one quarter of the width of the strip.

According to a second also particularly advantageous embodiment of the invention, two laser scanners are used, which are fixed above the pickled strip at a distance from its edges of between one quarter and one third of its width and that are connected to another device of the same type, which is attached to it above the center of the strip.

Finally, the apparatus control system is advantageously, also able to send data to a general control system controlling management of the strip processing installations downstream and/or upstream of said pickling apparatus.

Other advantageous characteristics of the invention are detailed in the following description of certain embodiments given as examples and shown on the attached drawings:

DESCRIPTION OF THE INVENTION

Identical elements shown in FIGS. 1 to 6 are identified by identical numerical references.

The continuous pickling line apparatus 1 shown in FIG. 1 has previously been described in the reference to the prior art above.

Furthermore, the fragmentation system 12 shown in FIG. 2, the pickling system 12 shown in FIG. 3, as well as the rinsing unit 15 shown in FIG. 4 have also been described previously in the reference to the prior art above.

Figure 5:
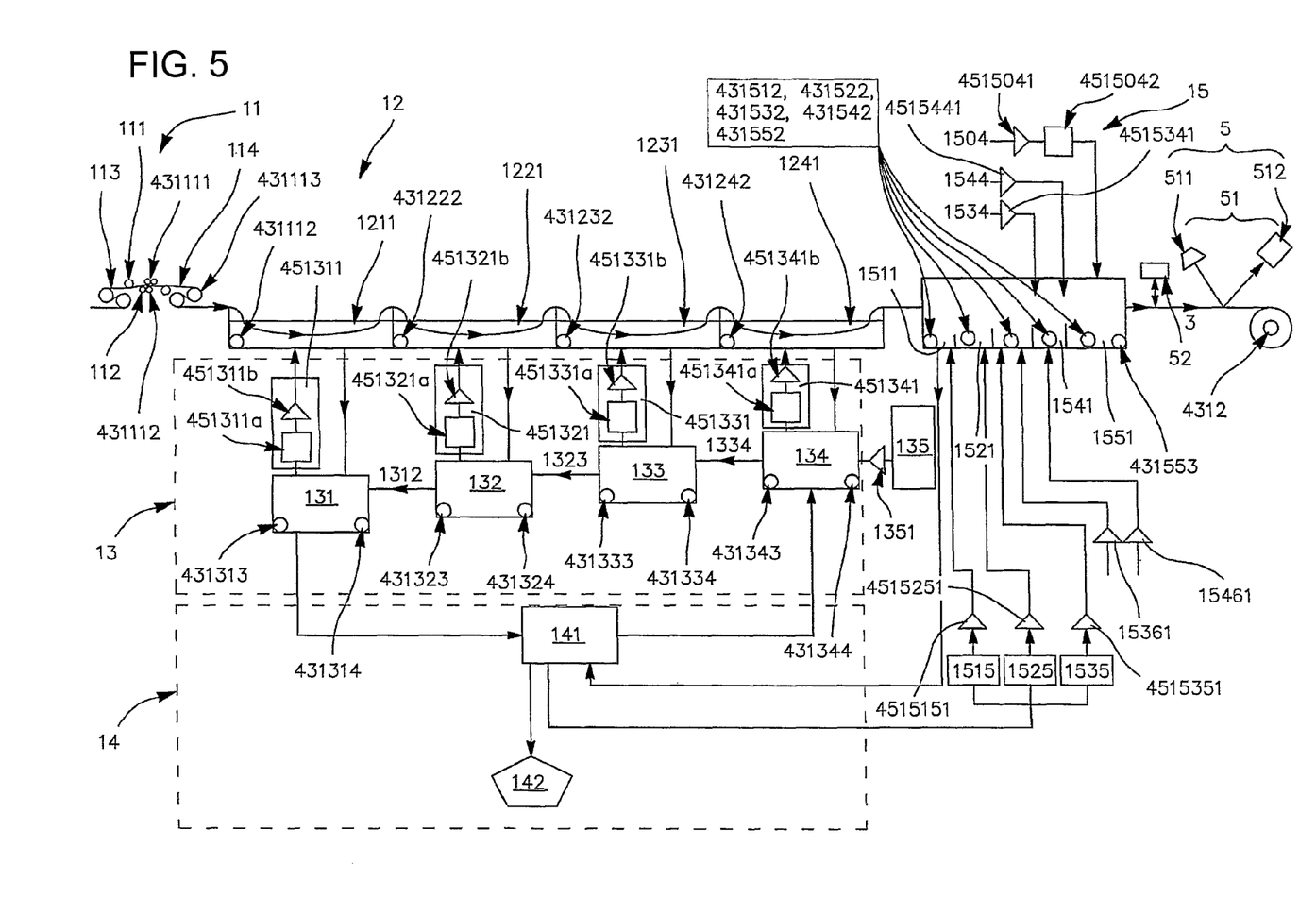
FIG. 5 is a schematic drawing of an example of the continuous pickling line apparatus according to the invention.

The pickling installation according to the invention shown in FIG. 5 in particular includes:
- a fragmentation system 11 for the oxide that has formed on the surface of the steel strip 2 during hot rolling,
- a pickling system 12 for the acid corrosion of the oxides, and
- a rinsing unit 15 to remove the acid (and in particular hydrochloric acid) and iron chlorides present on the surface of the strip.

The fragmentation system 11, the pickling system 12 and the rinsing unit 15 are arranged in series in the pickling apparatus 1 according to the invention such that the strip 2 being pickled passes in turn, as it moves continuously through the pickling apparatus 1, the fragmentation system 11, then the pickling system 12 and the rinsing unit 15.

The fragmentation system 11 useable in the apparatus according to the invention may in particular be the one shown in FIG. 2, which comprises notably:
- actuators 45111, 451112 controlling overlapping 1112 of the work rolls 111 via the height difference 1111 between the lowest work roll(s) and the highest work roll(s) between which the strip 2 is leveled, and
- an actuator 451113 controlling the traction 451113 exercised between the input tensioners 113 and the output tensioners 114.

The pickling system 12 recommended for use in the apparatus 1 according to the invention shown in FIG. 5 is the one shown in FIG. 3, to which is added:
- an acid top-up system 135 at the last storage tank 134 encountered in the running direction 3 of the strip 2, and
- a set of means for measuring the pickling adjustment parameters 431212, 431222, 431232, 431242, 431313, 431323, 431333, 431343, 431314, 431324, 431334, 431344 and
- a set of actuators 451311, 451311a, 451311b, 431321, 451321a, 451321b, 451331, 451331a, 451331b, 431341, 451341a, 451341b acting on said pickling adjustment parameters.

The measurement means 431212, 431222, 431232, 431242, 431313, 431333, 431343, 431314, 431324, 431334, 431344 of the pickling adjustment parameters include:
- means for measuring the temperature 431212, 431222, 431232, 431242 of the pickling solution 1211, 1221, 1231, 1241 contained in the different pickling tanks 121, 122, 123, 124,
- means for measuring the density 431313, 431323, 431333, 431343 of the pickling solution 1211, 1221, 1231, 1241 in said storage tanks 131, 132, 133, 134, and means for measuring the conductivity 431314, 431324, 431334, 431344 of the pickling solution 1211, 1221, 1231, 1241 in said storage tanks 131, 132, 133, 134.

In the pickling apparatus 1 according to the invention, the actuators 451311, 451311a, 451311b, 451321, 451321a, 451321b, 451331, 451331a, 451331b, 451341, 451341a, 451341b able to act on the pickling adjustment parameters include pumping and reheating units 451311, 451321, 451331, 451341 that are each connected to a pickling tank 121, 122, 123, 124 and that each include:

- a heat exchanger 451311a, 451321a, 451331a, 451341a to control the temperature of the pickling solution 1211, 1221, 1231, 1241 in the recirculation circuit 132 of the pickling system 12, and
- a pump 451311a, 451321b, 451331b, 451341b to control the flow of pickling solution 1211, 1221, 1231, 1241 in the recirculation circuit 13 of the pickling system 12, and
- a pump 451351 to control the flow of extra acid 135 in the last storage tank 134 encountered in the running direction 3 of the strip 2.

The rinsing system useable in the apparatus according to the invention shown in FIG. 4 may be the one shown in FIG. 4, which comprises:

- a plurality of spray bars 151, 152, 153, 154, 155 supplied with demineralized water for rinsing, which are arranged such that they can spray both faces 21, 22 of the strip 2 with water,
- a plurality of flow tanks 1511, 1521, 1531, 1541, 1551, each of which is arranged beneath the spray bars 151, 152, 153, 154, 155, the water overflowing into its neighboring tank forming a cascade flowing in the direction opposite to the running direction 3 of the strip 2,
- roller drier devices 1501, 1502 placed at the entrance and exit of the rinsing unit 15, as well as roller drier devices 1512, 1523, 1534, 1545 placed between each battery of bars 151, 152, 153, 154, 155.

The rinsing system 15 shown in FIG. 5 also includes (compared to the rinsing system 15 in the prior art shown in FIG. 4):

- a main demineralized-water top-up system 1504 to supply rinsing water to the spray bars 151, 152, 153, 154, 155 of the rinsing unit,
- two supplementary demineralized-water top-up devices 1534, 1544 to supply, as required, the third 153 and fourth 154 spray bars encountered in the running direction 3 of the strip 2,
- acid injection devices 1515, 1525, 1535 in the first flow tanks 1511, 1521, 1531 of the rinsing unit 15 encountered in the running direction 3 of the strip 2, and
- alkaline-product injection devices 1536, 1546 in the third 1531 and fourth 1541 flow tanks of the rinsing unit 15 encountered in the running direction 3 of the strip 2.

Furthermore, the rinsing system 15 of the apparatus shown in FIG. 5 includes measurement means 431512, 431522, 431532, 431542, 431552, 431553, 431554 of the rinsing adjustment parameters and actuators 4515151, 4515251, 4515351, 4515361, 4515461, 4515341, 4515441, 4515041, 4515042 able to act on these rinsing adjustment parameters.

The measurement means 431512, 431522, 431532, 431542, 431552, 431553, 431554 of the rinsing adjustment parameters enabling the activation of the rinsing device 15 include:

- pH measurement means 431512, 431522, 431532, 431542, 431552 for the rinsing water in the flow tanks 1511, 1521, 1531, 1541, 1551 of the rinsing units 15,
- conductivity measurement means 431553 for the rinsing water contained in the last flow tank 1551 encountered in the running direction 3 of the strip 2,
- temperature measurement means 431554 for the rinsing water contained in the last flow tank 1551 encountered in the running direction 3 of the strip 2.

The actuators 4515151, 4515251, 4515351, 4515361, 4515461, 4515341, 4515441, 4515041, 4515042 able to act on the rinsing parameters include:

- pumps 4515151, 4515251, 4515351 to control the flow of acid from said acid-injection devices 1515, 1525, 1535,
- pumps 4515361, 4515461 to control the flow of alkaline product from the alkaline-product-injection devices 1536, 1546,
- pumps 4515341, 4515441 to control the flow of demineralized water from the supplementary demineralized-water top-up devices 1534, 1544,
- a pump 4515041 to control the flow of demineralized water from the main demineralized-water top-up device 1504,
- a heat exchanger 4515042 to control the temperature of the demineralized water from the main demineralized-water top-up device 1504.

The apparatus 1 according to the invention also includes, at the output of rinsing and drying an inspection system 5 of the strip 2 that breaks down as follows:

- a surface appearance inspection system 51, and
- a surface condition measurement system 52.

The surface appearance inspection system 5 of the strip 2 includes advantageously:

- a lighting device 511 for the running strip 2, which is attached to
- an image capture device 512,
- an image processing function 513
- a grey-threshold or contour detection function 514,
- a photometric and morphological characterization and extraction function 515 for suspect zones, and
- an identification and classification function 516 for suspect zones with reference to an image library, this function 516 making it possible to distinguish between "under pickling" defects, "over pickling" defects or even intrinsic defects in the steel strip 2, and the absence of any defects.

The surface condition measurement system 52 includes advantageously:

- an optical device 521 for the continuous examination of at least one line of the running strip 2,
- a signal processing function 522, and
- a learning-based classification function 523 with reference to a database, for suspect zones, this function 523 making it possible to distinguish between defects and an absence of defects.

The surface condition measurement system 52 makes it possible to continuously examine at least one line situated in the middle of the width of the running strip 2, and preferably three lines where one is situated in the middle of the strip width and the two others in a zone situated between one third and one quarter of the strip width from each edge of the pickled strip.

Figure 6:
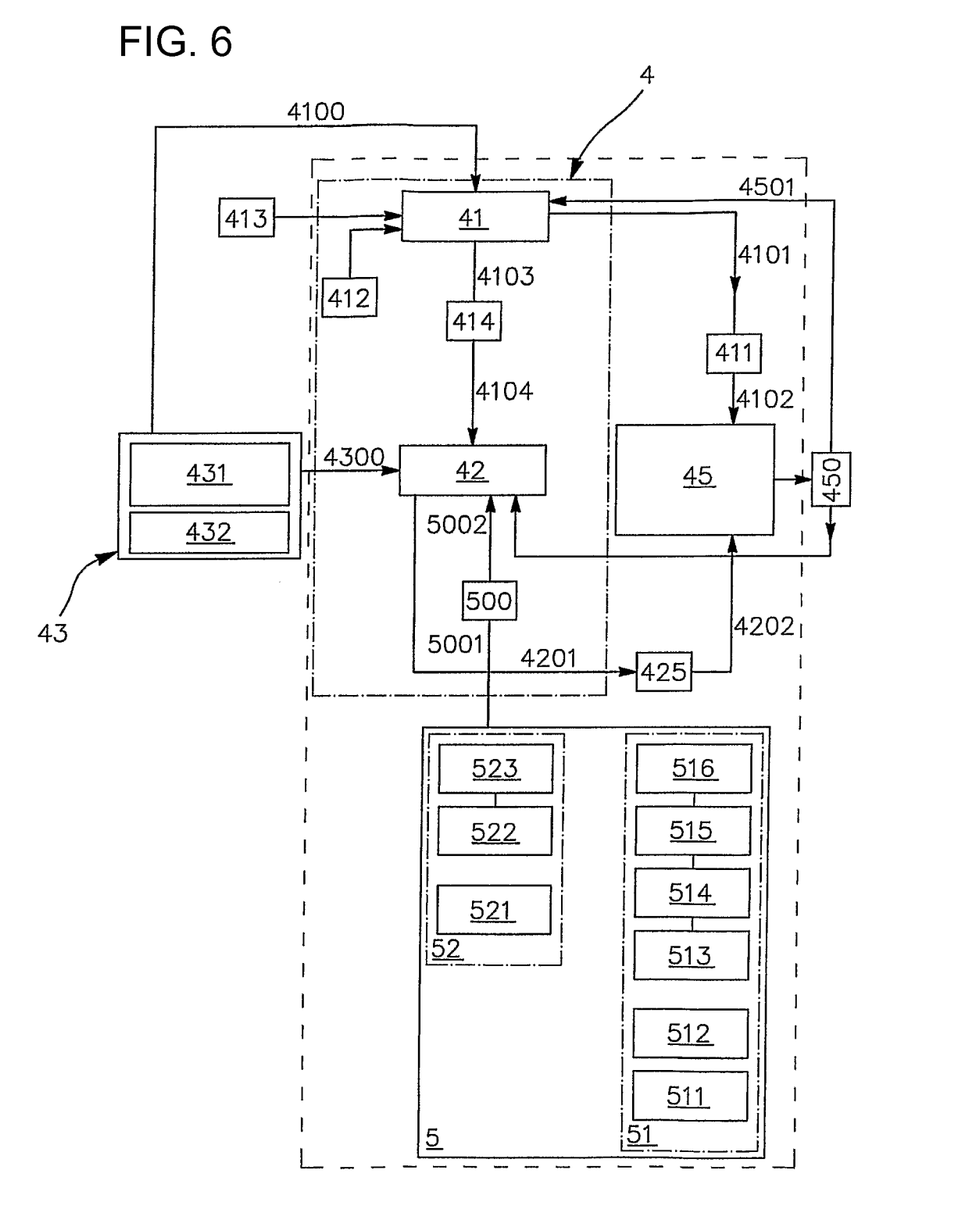
FIG. 6 is a diagram showing the different phases of the global control process of the method according to the invention.

All of the measurement means 43 of the apparatus 1 and all of the actuators 45 of the apparatus 1 are controlled by a centralized control system 4, which enables the control of pickling by means of a global process that includes:

- the continuous measurement 43101, 43102 of at least some of the pickling adjustment parameters, said measurement being implemented during pickling;

the continuous calculation 43200 of at least some of the pickling adjustment parameters, said calculation being implemented during pickling;

a prior preparation phase 4101, 4102 which is implemented upstream or at the start of pickling, during which the global control process 4000 defines 4101 and sends 4102 pre-adjustment instructions 411 to all of the actuators 45 using an analytical model, which may be associated with a predictive control system a command phase 4201, 4202 which is implemented during pickling, during which the global control process 4000 defines 4201 and sends 4202 optimized command instructions to all of the actuators using a predictive control system; and the continuous inspection 5001, 5002 of the surface of the strip 2, which results in the definition 5001 and sending 5002, in the case of under-pickling, of an alarm instruction (500) to the command phase 4201, 4202, which reduces the running speed V of the strip 2 stepwise to a corrected running speed $V_{cor}$, the stepwise reduction in the running speed V being effected until the condition of the strip 2 is deemed to be satisfactory during the inspection 5001, 5002 of the surface of the strip 2.

The preparation module 41 performs the preparation phase 4101, 4102 of the method according to this invention, which includes advantageously the following operations:

receiving status data 450 from 4501 the actuators 45, operating data 413, and target values 412 for the adjustment parameters established by the analytical model to optimize pickling of the strip 2;

establishing 4101 pre-adjustment instructions 411 for each actuator 45;

sending 4102 pre-adjustment instructions 421 to each actuator 45;

establishing 4103 the input data 414 for the command phase 4201, 4202;

sending 4104 said input data 414 to the command phase 4401.

A calculation module performs the calculation phase 43200 for the different concentrations of acid 4321 and iron 4322 in the pickling solution 1211, 1221, 1231, 1241 flowing in the pickling system 12.

The command module 42 performs the command phase 4401, 4402, which includes the following operations:

receiving continuously and in real time status data 450 from 4502 the actuators 45, information from 4300 the measurement and calculation means 43, and input data 414 for the command phase 4201, 4202 established during the preparation phase 4101, 4102;

establishing 4201 command signals 425 optimized for each actuator 45;

sending 4202 said command signals 421 to the actuators 45.

The surface inspection system 5 performs the surface inspection phase of the strip 2 at the output of the pickling apparatus, by optical inspection 5001 of the appearance of the surface of the strip 2 firstly, and by measuring the variations in the condition of the surface of the strip 2.

The invention claimed is:

1. A pickling method, comprising:

feeding a metal strip through a pickling line apparatus, the pickling line apparatus including, successively, a fragmentation stage for oxides formed on a surface of said strip during hot rolling, an acid pickling stage, a rinsing stage for the strip, and a drying stage;

thereby driving the strip at a running speed V in the pickling line apparatus in a longitudinal running direction perpendicular to a width of the strip, controlling the running speed V by an uncoiling and coiling unit, and controlling each of the stages of pickling by way of actuators configured to act on the adjustment parameters of the pickling line, wherein an action or absence of action of an actuator on a given adjustment parameter is identified by a status datum; and implementing a global control process for pickling, including:

a prior preparation phase upstream or at a start of pickling, wherein the global control process defines and sends pre-adjustment instructions to all of the actuators using an analytical model, which may be associated with the predictive control system;

carrying out continuous measurement of at least some of the pickling adjustment parameters, the measurement being implemented during pickling;

a command phase which is implemented during pickling, during which the global control process defines and sends optimized command instructions to all of the actuators using a predictive control system;

continuously calculating at least some of the pickling adjustment parameters during pickling; and continuously inspecting the surface of the strip, and thereby defining and sending, in the event of under-pickling, an alarm instruction to the command phase, for reducing stepwise the running speed V of the strip to a corrected running speed, and continuing the stepwise reduction of the running speed V until the defect is no longer detected and no longer triggers the alarm instruction, and also, the continuously inspecting the surface of the strip detecting a rinsing of the strip, if defective rinsing is detected, adjusting a pH of the rinsing water in steps until the defect is no longer detected.

2. The method according to claim 1, wherein the predictive model of the global control process corrects the command instructions sent to all of the actuators apart from the running speed V of the strip, as a function of the correction made to the running speed $V_{cor}$, and such as to maintain a quality of the evaluation made during inspection of the surface of the strip.

3. The method according to claim 1, wherein the step of inspecting the strip comprises:

optically inspecting an appearance of the surface of the strip; and measuring a variation of at least one characteristic of the surface condition of the strip.

4. The method according to claim 3, wherein the step of optically inspecting the appearance of the surface of the strip and the step of measuring the variation of the surface condition of the strip include learning suspect zones with reference to a library of images and/or data enabling a distinction to be made between over-pickling defects, under-pickling defects, or an absence of defects.

5. The method according to claim 1, wherein the calculating step comprises defining acid and iron concentrations in a pickling solution used during acid pickling.

6. The method according to claim 1, wherein the preparation phase comprises:

receiving status data from the actuators, operating data, and target values for the adjustment parameters established by the analytical model to optimize pickling of the strip;

establishing pre-adjustment instructions for each actuator and sending the pre-adjustment instructions to each actuator;

establishing input data for the command phase and sending the input data to the command phase.

7. The method according to claim 6, wherein the analytical model includes an analytical sub-model associated with each actuator to define the pre-adjustment instruction for the adjustment parameter on which the related actuator acts.

8. The method according to claim 1, wherein the command phase comprises:
receiving continuously and in real time status data from the actuators, information from the measurement and calculation means, and input data for the command phase established during the preparation phase;
establishing command signals optimized for each actuator, and sending the command signals to the actuators.

9. The method according to claim 8, wherein the predictive control system includes a primary adjustment loop to check the optimum operation of each actuator on the command instruction sent to it.

10. A continuous line apparatus for pickling a hot-rolled metal strip running continuously in the apparatus, the apparatus comprising:
a fragmentation system for oxides formed on a surface of the strip, said oxide fragmentation system being adjustable by way of fragmentation adjustment parameters;
a pickling system, adjustable by way of pickling adjustment parameters; and
a rinsing system, adjustable by way of rinsing adjustment parameters;
a set of measuring and calculating devices for measuring and calculating the adjustment parameters of the apparatus;
a set of actuators configured to act on the adjustment parameters of said apparatus;
a centralized command system configured to optimize pickling of the metal strip, said command system including:
a preparation module connected to receive information from all of said measuring and calculating devices and said actuators, and configured to define and send pre-adjustment instructions to all of said actuators;
a command module connected to receive information from all of said measuring and calculating devices and said actuators, and configured to define and send optimized command instructions to all of said actuators; and
an inspection system for inspecting the strip at an output of said rinsing system, said inspection system being able to define and send an alarm instruction to said command module to act on the running speed V of the strip;
said inspection system configured for detecting defective rinsing of the strip and in an event of a detection of defective rinsing, making a stepwise pH adjustment of the rinsing water, until the defect is no longer detected.

11. The apparatus according to claim 10, wherein said inspection system is enabled to define and send a command instruction to said command module to act on the rinsing adjustment parameters.

12. The apparatus according to claim 10, wherein said set of measuring and calculating devices comprises:
a set of measurement means including measurement means for the running speed V of the strip, measurement means for an oxide fragmentation adjustment parameters, measurement means for at least some of the pickling adjustment parameters, and measurement means for the rinsing adjustment parameters; and
calculation means for at least some of the pickling adjustment parameters.

13. The apparatus according to claim 12, wherein said calculation means are enabled to determine a concentration of acid and ferrous ions in the pickling solution used in the pickling system.

14. The apparatus according to claim 12, wherein:
said rinsing unit includes a plurality of spray bars supplied with demineralized water for rinsing and disposed to spray water onto the strip, and a plurality of flow tanks each disposed underneath said spray bars; and
said measurement means for the rinsing adjustment parameters include pH measurement means for the rinsing water in the flow tanks of the rinsing unit, conductivity measurement means, and temperature measurement means for the rinsing water contained in a last flow tank, as seen in a running direction of the strip.

15. The apparatus according to claim 14, wherein:
said rinsing unit includes a main demineralized-water top-up device for supplying said spray bars, supplementary demineralized-water top-up devices for supplying third and fourth spray bars, as seen in the running direction of the strip, acid injection devices in first flow tanks of said rinsing unit, as seen in the running direction of the strip, and alkaline-product injection devices in a third flow tank and a fourth flow tank of said rinsing unit, as seen in the running direction of the strip; and
said actuators for acting on the rinsing parameters include a pump controlling a flow of demineralized water from said main demineralized-water top-up device, a heat exchanger controlling a temperature of the demineralized water from said main demineralized-water top-up device, and pumps controlling a flow of demineralized water from said supplementary demineralized-water top-up devices, pumps controlling a flow of acid from said acid injection devices, and pumps controlling a flow of alkaline-product from said alkaline-product injection devices.

16. The apparatus according to claim 10, wherein said set of actuators comprises fragmentation actuators configured to act on the oxide fragmentation adjustment parameters, pickling actuators configured to act on the pickling adjustment parameters, and rinsing actuators configured to act on the rinsing adjustment parameters.

17. The apparatus according to claim 10, wherein said surface inspection system comprises:
a surface appearance inspection system for inspecting a surface appearance of the strip; and
a surface condition measurement system for measuring a surface condition of the strip.

18. The apparatus according to claim 17, wherein said surface appearance inspection system comprises:
a lighting device for the running strip, which is attached to an image capture device
an image processing function,
a grey-threshold or contour detection function,
a photometric and morphological characterization and extraction function for suspect zones, and
a suspect-zone identification and classification function.

19. The apparatus according to claim 17, wherein said surface condition measurement system is configured to measure variations in at least one characteristic of a surface condition of the strip.

20. The apparatus according to claim 17, wherein said surface condition measurement system comprises:
at least one optical device for a continuous examination of at least one line of the strip;
a signal processing function; and
a suspect-zone classification function.

21. The apparatus according to claim 20, wherein said optical device is a device selected from the group consisting of a laser scanner device, a scatter laser device, and an optical axial chromatic aberration device.

22. The apparatus according to claim 20, wherein said surface condition measurement system comprises two optical devices fixedly mounted above the pickled strip, at a distance from edges of the strip of between one quarter and one third of width of the strip, and connected to another device of the same type fixedly mounted above a center of the strip.

23. The apparatus according to claim 17, wherein said surface condition measurement system comprises two optical devices disposed above the running strip, at a distance from edges of the strip of between one quarter and one third of a width of the strip.

24. The apparatus according to claim 10, wherein said control system of the apparatus is configured to send data to a general control system controlling management of the processing installation for the strip downstream and/or upstream of the pickling apparatus.

\* \* \* \* \*